US00PP25120P3

(12) United States Plant Patent
Pavlich

(10) Patent No.: US PP25,120 P3
(45) Date of Patent: Nov. 25, 2014

(54) *BEGONIA* PLANT NAMED 'COOL BREEZE GLACIER'

(50) Latin Name: ***Begonia* hybrid**
Varietal Denomination: Cool Breeze Glacier

(71) Applicant: Terra Nova Nurseries, Inc., Canby, OR (US)

(72) Inventor: John C. Pavlich, Olympia, WA (US)

(73) Assignee: Terra Nova Nurseries, Inc., Canby, OR (US)

( * ) Notice: Subject to any disclaimer, the term of this patent is extended or adjusted under 35 U.S.C. 154(b) by 35 days.

(21) Appl. No.: 13/986,393

(22) Filed: Apr. 26, 2013

(65) Prior Publication Data

US 2014/0325719 P1 Oct. 30, 2014

(51) Int. Cl.
*A01H 5/02* (2006.01)

(52) U.S. Cl.
USPC ..... Plt./343

(58) Field of Classification Search
CPC ..... A01H 5/0238
USPC ..... Plt./343
See application file for complete search history.

*Primary Examiner* — June Hwu
*Assistant Examiner* — Keith Robinson
(74) *Attorney, Agent, or Firm* — Klarquist Sparkman, LLP

(57) ABSTRACT

A new and distinct form of *Begonia* plant characterized by broad, rugose, and shallowly palmately lobed leaves, showy interveinal silvering, red leaf backs, a bushy habit, clusters of cherry pink flowers in winter to early spring, and excellent vigor.

1 Drawing Sheet

Botanical denomination: *Begonia* hybrid.

Variety designation: 'Cool Breeze Glacier'.

Parentage: *Begonia hemsleyana*×*Begonia* U489.

Cross Reference to: *Begonia* 'Cool Breeze Pewter' (U.S. Plant patent application Ser. No. 13/987,232) and 'Cool Breeze Rouge' (U.S. Plant patent application Ser. No. 13/986,388).

BACKGROUND

The present invention relates to a new and distinct cultivar of *Begonia*, of the family Begoniaceae, and given the cultivar name, 'Cool Breeze Glacier'. This plant originated from planned breeding program for a colorful series of landscape *Begonia*. The new cultivar originated from a cross between *Begonia hemsleyana*, as the seed parent, and *Begonia* U489, as the pollen parent. This selection is uniquely characterized by:

1. broad, rugose, and shallowly palmately lobed leaves,
2. showy interveinal silvering,
3. red leaf backs,
4. a bushy habit,
5. clusters of cherry pink flowers in winter to early spring, and
6. excellent vigor.

Compared to the seed parent *Begonia hemsleyana*, an unpatented plant, the new cultivar has leaves shallowly palmately lobed rather than palmately compound.

Compared to the pollen parent, *Begonia* U489, an unpatented plant, the new cultivar is broader in habit, better branched, and with leaves that are more rugose.

Compared to *Begonia* 'Silver Splendor', U.S. Plant Pat. No. 21,946, the new cultivar has broad leaves that are shallowly lobed rather than deeply cut leaves.

Compared to *Begonia* 'Metallic Mist' U.S. Plant Pat. No. 19,567, the new cultivar is taller, with leaves more rugose, pinker flowers, and green rather than red leaf veins.

Compared to *Begonia* 'Cool Breeze Pewter', the new cultivar has interveinal white silvering on the leaf topsides rather that pewter leaf tones with a deep green spot at the leaf base.

Compared to *Begonia* 'Cool Breeze Rouge', the new cultivar has interveinal white silvering on the leaf topsides rather that pewter leaf tones that blush rouge and with a deep green spot at the leaf base.

The new variety has been reproduced only by asexual propagation (leaf cuttings and tissue culture). Each of the progeny exhibits identical characteristics to the original plant. Asexual propagation by micropropagation as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the flowers and leaf of *Begonia* 'Cool Breeze Glacier'.

FIG. 2 shows a 1-year old plant in a growing in a one gallon container in January in Canby. Oreg.

DETAILED PLANT DESCRIPTION

The following is a detailed description of the new *Begonia* cultivar based on observations of one-year-old specimens grown in one gallon containers outside in shade in early November in Canby, Oreg. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, 5th edition, 2007.

Plant:

*Type*.—Herbaceous rhizomatous perennial.

*Form*.—Clumping, caulescent.

*Cold hardiness*.—USDA Zone 10.

*Size*.—Grows to 28 cm tall and 50 cm wide.

*Vigor*.—Excellent.

*Roots and rooting*.—Roots appear on leaf cuttings in 2 weeks; fine, fibrous, and white in color.

Stem:

*Type*.—Upright.

*Size*.—Grows to 15 cm long and 10 mm wide.

*Internodes*.—From 1.5 to 3 cm long.

*Lateral branches*.—None.

*Surface*.—Pubescent.

*Color*.—Greyed Purple 187A to 187B.

Leaf:

*Type*.—Simple.

*Arrangement*.—Basal and alternate.

*Number*.—About 160.

*Leaf strength*.—Excellent.

*Shape*.—Broadly ovate to orbicular.

*Lobing/division*.—Palmately 7 lobed.

*Venation*.—Palmate, Green N137D on topside, bottom side Greyed Green 195A and Greyed Brown 197B.

*Margins*.—Crenulate, revolute.

*Apex*.—Acuminate.

*Base*.—Sagittate to cordate and overlapping.

*Blade size*.—Grows to 16 cm wide and 17 cm long.

*Surface texture*.—Pubescent on top and bottom.

*Stipules*.—Deciduous, ovate-lanceolate, 25 mm long and 12 mm wide, apex acuminate and cuspidate, base clasping, entire, back side pubescent, inside glabrous, both sides Greyed Orange 174B.

*Petiole description*.—Grows to 16 cm long and 7 mm wide, succulent, pubescent, Greyed Orange 177A.

*Leaf color*.—Top side closest to Green136A along veins and Greyed Green 188C interveinally; bottom side Greyed Green 194A tinted Greyed Purple 187B.

Inflorescence:

*Type*.—Axillary, bisexual, cymose.

*Number of flowers per cyme*.—About 4.

*Peduncle description*.—Grows 3 cm long and 2 mm wide, sparsely pubescent, fleshy, of good strength, Greyed Purple 187A; with 2 opposite, dehiscent petiolate leaf-bracts below each cyme, which grow to 6 mm wide and 12 mm long, margins entire, tip apiculate, back side pubescent, inside glabrous, both sides Greyed Red 182B

*Pedicel description*.—Grow to 20 mm long, 1.5 mm wide, fleshy, of good strength, pubescent, Red Purple 63C on staminate flowers, Greyed Purple 187D on pistillate flowers.

*Bloom period*.—Late fall to early winter in Canby, Oreg.

Flower bud:

*Size*.—Staminate flowers 13 mm long and 11 mm wide prior to opening; pistillate flowers are 25 mm deep and 21 mm wide prior to opening.

*Shape*.—Teardrop.

*Surface texture*.—Pubescent.

*Color*.—Red Purple 68B on tepal area, Greyed Orange 174A on ovary.

Flower:

*Type*.—Monoecious, bilaterally symmetrical.

*Pistillate flower*.—Grows to 21 mm deep and 32 mm wide overall; 5 fleshy tepals, grow to 18 mm long and 12 mm wide, broadly elliptical, tip and base obtuse, margins entire, glabrous on inside and pubescent on outside, outer tepals Red Purple 63C on inside and 68B outside, inner tepals Red Purple 62B on both sides except up the middle on back side where 63C; pistil 1, 20 mm long, ovary to 20 mm wide and 12 mm deep, three winged, two equal and one longer, Greyed Purple 183C, style 2 branched, 2 mm long and Greyed Yellow 161B, stigma 2 branched and twisted, stigma 6 mm deep and 8 mm wide overall, Green Yellow 1C.

*Staminate flower*.—12 mm deep and 38 mm wide, 4 tepals, 2 larger outer tepals 23 mm long and 11 mm wide, cupped, broadly elliptical, margin entire, tip obtuse, base cuneate, pubescent outside and glabrous inside, Red Purple 62C inside and 59D outside; inner tepals grow to 18 mm long and 8 mm wide, oblanceolate, entire, tip obtuse, base attenuate, both sides Red Purple 73C; stamen many in a globular head 7 mm in diameter, filament 2 mm long, anthers 2 mm long and Red Purple 65D, anthers and pollen Yellow 12C.

*Fragrance*.—None.

*Lastingness*.—A cyme blooms for about 4 weeks on the plant, flowers are self-cleaning.

Fruit and seed: None, sterile.

Diseases and pests: The new cultivar is typical to the genus. No known resistances to pests or diseases. No problems have been found in Canby, Oreg.

I claim:

1. A new and distinct form of *Begonia* plant as hereby illustrated and described.

* * * * *

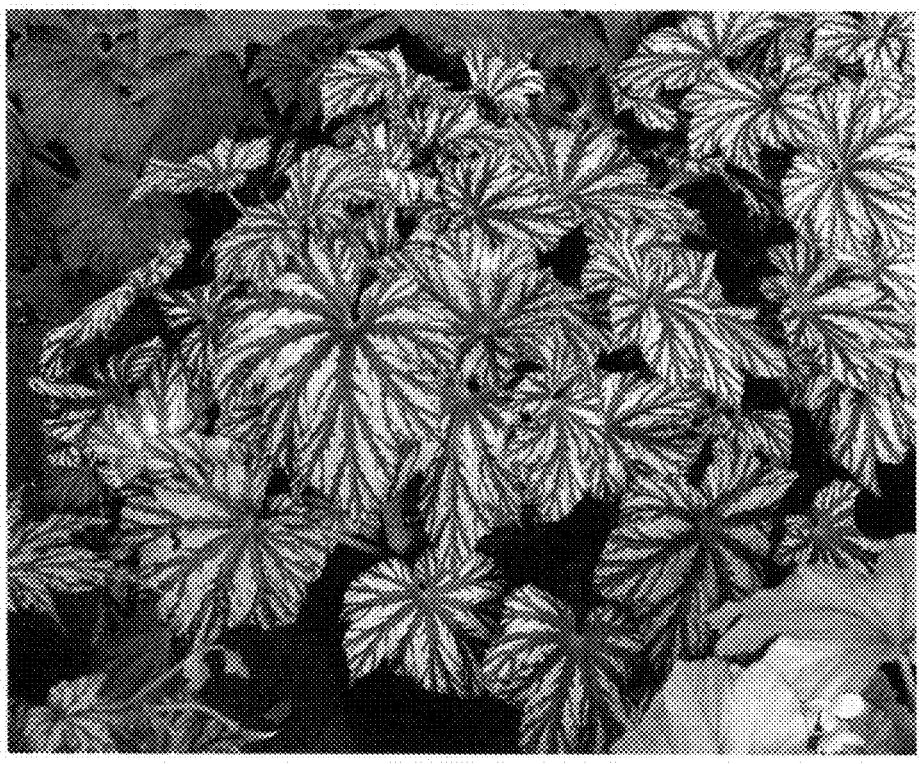

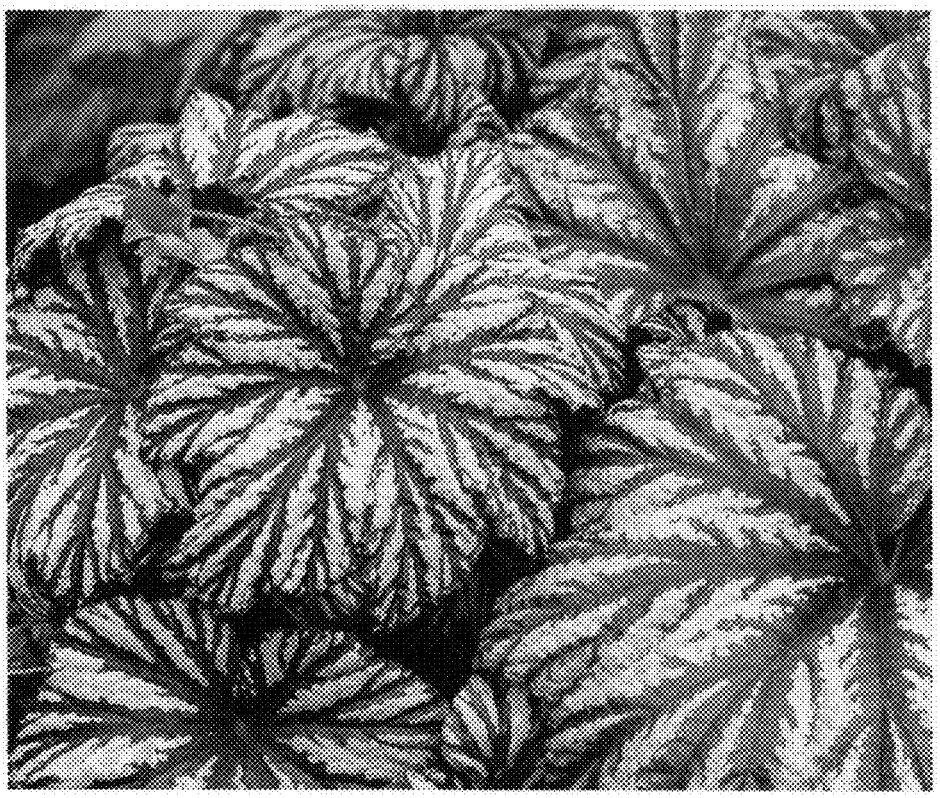
FIG. 1 above, FIG. 2 below